United States Patent
Su

(10) Patent No.: US 11,883,015 B2
(45) Date of Patent: Jan. 30, 2024

(54) RETRACTOR USED TO ASSIST CUFF IMPLANTATION, TISSUE REPOSITIONING AND OTHER APPLICATIONS

(71) Applicant: Ning Miao Su, Irvine, CA (US)

(72) Inventor: Ning Miao Su, Irvine, CA (US)

(73) Assignee: Ning Miao Su, Irvine, CA (US)

( * ) Notice: Subject to any disclaimer, the term of this patent is extended or adjusted under 35 U.S.C. 154(b) by 0 days.

(21) Appl. No.: 16/139,087

(22) Filed: Sep. 23, 2018

(65) Prior Publication Data

US 2020/0093470 A1  Mar. 26, 2020

(51) Int. Cl.
*A61B 17/02* (2006.01)
*A61B 17/00* (2006.01)

(52) U.S. Cl.
CPC .... *A61B 17/02* (2013.01); *A61B 2017/00424* (2013.01)

(58) Field of Classification Search
CPC ...................... A61B 17/02; A61B 2017/00424
See application file for complete search history.

(56) References Cited

U.S. PATENT DOCUMENTS

| | | | |
|---|---|---|---|
| 2009/0216089 A1* | 8/2009 | Davidson | A61B 17/02 600/235 |
| 2010/0005630 A1* | 1/2010 | Gitman | B25G 1/102 606/167 |
| 2010/0240005 A1* | 9/2010 | Gordon | A61C 3/00 433/93 |
| 2014/0128684 A1* | 5/2014 | Carlson | A61B 17/02 600/217 |
| 2016/0331407 A1* | 11/2016 | Anderson | A61B 17/02 |
| 2017/0071587 A1* | 3/2017 | Harshman | A61B 1/32 |
| 2019/0216568 A1* | 7/2019 | Zadeh | A61B 90/08 |

FOREIGN PATENT DOCUMENTS

DE      202013000103 U1 *  5/2013  ............ A61B 17/02

* cited by examiner

*Primary Examiner* — Julianna N Harvey

(57) ABSTRACT

A retractor is designed to assist in cuff implantation procedure. It has a flat non-cutting retracting end at the distal. Its function is to isolate tissue of interest, to make access, and to retract tissue for cuff placement and removal while protecting critical tissue at the surgical site.

16 Claims, 5 Drawing Sheets

A. horizontal plane
U. preferred length of the present retractor
W. passive grip handle
X. main shaft of the retractor
Y. supporting shaft of the retractor
Z. non-cutting retracting end A. horizontal plane
U. preferred length of the present retractor
W. passive grip handle
X. main shaft of the retractor
Y. supporting shaft of the retractor
Z. non-cutting retracting end

A. horizontal plane
B. upper surface of the handle
C. finger rest on upper surface
D. upper surface supporting shaft
E. retractor tip
F. lower surface supporting shaft
G. finger rest on lower surface
H. lower surface of the handle

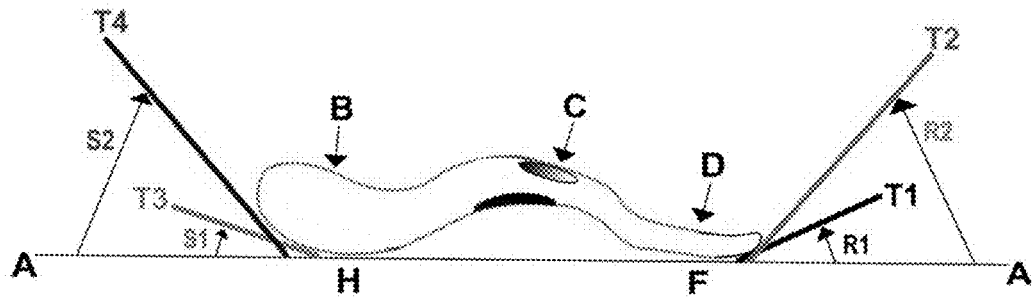

FIG. 3

A. horizontal plane
B. upper surface of the handle
C. finger rest on upper surface
D. upper surface supporting shaft
H. lower surface of the handle passing horizontal plane
F. lower surface supporting shaft passing horizontal plane
T1. Tangent line of the curved tip closer to point F
T2. Tangent line of the curved tip away from point F
T3. Tangent line of the handle closer to point H
T4. Tangent line of the handle away from point H
R1. Angle between T1 and plane A
R2. Angle between T2 and plane A
S1. Angle between T3 and plane A
S2. Angle between T4 and plane A

Fragmentary Plan View of Retractor Tip
I. top view of retracting end
J. side view of retracting end

K. Top Plan View of Retractor
L. retracting end
M. finger rest
N. main shaft
O. handle
P. supporting shaft Perspective View of the Retractor

RETRACTOR USED TO ASSIST CUFF IMPLANTATION, TISSUE REPOSITIONING AND OTHER APPLICATIONS

FIELD OF INVENTION

The retractor described in this patent has a function in assisting cuff placement during surgical implantation. The cuffs are used to enclose internal organ or tissue of interest, and the applications installed at the inner surface of the cuffs can give electrical stimulations or exert therapeutic effects to the surrounded tissue. This retractor offers control and precision to the users in utilizing this instrument to retract and make access while protecting nearby soft tissue and structures at the surgical site.

BACKGROUND OF THE INVENTION

When performing surgical implantation using cuffs, there are many concerns and disadvantages in using prior art retractors to clean out surrounding connective tissue, to isolate tissue of interest, and to facilitate the placement and removal of the cuff. The purposes of this patent are to provide a surgical instrument to assist and facilitate cuff placement and removal, to retract and protect soft tissue without damages to surrounding organs, muscles, nerves and veins, to avoid the need of using extra retractors during cuff placement and removal, to give better access for surgical procedures by improving visualization at the surgical site. No prior art retractors are able to offer as many degrees of freedom this present retractor offers. With six degrees of freedom added to the design of this retractor, it improves the effectiveness of this surgical instrument, and provides a comfort grip and protection to its users.

SUMMARY OF THE INVENTION

This patent relates to a retractor to assist in cuff placement around tubular body tissue such as nerves, veins, muscles, intestines, fallopian tubes and etc. The retractor can also be used in nerve repositioning and in various surgical procedures to hold back soft tissue and make access. A variation of this retractor can assume purposes in prosthesis trainings, rehabilitation, and other applications.

DESCRIPTION OF THE DRAWINGS

FIG. 3 This is the side elevational view of the present retractor having its lowest points H and F at the lower surfaces of the handle and the supporting shaft passing a horizontal plane A. Two tangent lines T1 and T2 are shown at the curved surface of the retracting tip along with the angles R1 and R2 related to plane A. Two tangent lines T3 and T4 are shown at the lower surface of the handle along with the angles S1 and S2 related to the same plane A.

FIG. 4 K through O, shows the top plan view, and segments of the present retractor.

DETAILED DESCRIPTION OF THE INVENTION

Figure 1:
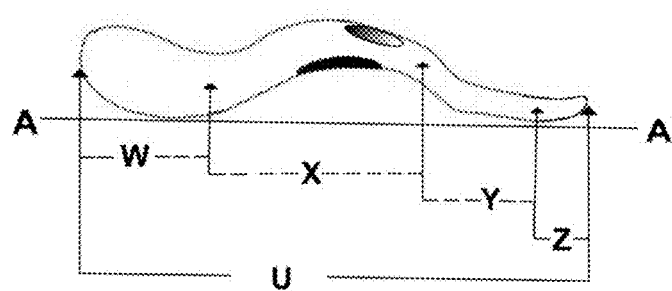
FIG. 1 shows the dimension and four segments of the present retractor. W: handle X: main shaft Y: integral supporting shaft Z: retracting end
Figure 2:
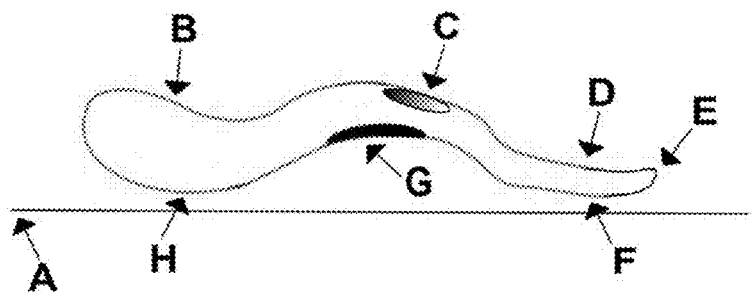
FIG. 2 is the side elevational view of the present retractor.

This patent describes a surgical retractor used to make access, to hold back and protect soft tissue, and to avoid damages to the adjacent vital organ and structures. This retractor is designed to assist in cuff placement during implantation and cuff removal due to cuff implant failure. FIG. 1 and FIG. 2 are the diagrams of the retractor described in this patent. The retractor is comprised of four segments, a rounded passive grip handle, and a main shaft with 2 finger rests, an integral supporting shaft, and a retracting end at the distal. The most preferred length U of the retractor is 15 cm. The preferred diameter of the handle W is between 12 mm and 16 mm, and the preferred diameter of the main shaft X is between 9 mm and 12 mm. The integral supporting shaft Y extends out of the main shaft and gradually transition to a more flatten profile where the retracting end Z of the retractor curves upward from this point.

The rounded handle fits passively between the thumb and the index finger. The advantage of this handle is that it does not require strength to hold and stabilize, and thus controlling the movement of the retracting end becomes easier for its users. The main shaft is extended from the handle in an upward direction. It is constructed as three degrees of freedom bend. In the main shaft, there are 2 finger rests C and G shown in FIG. 2. C is located on the upper surface of the shaft for the index finger to rest, and G is situated at the lower surface of the shaft for the side of the middle finger to support. Extended out of the main shaft is the integral supporting shaft that is curved out in a slightly downward direction. The upward extension of the main shaft and the downward extension of the supporting shaft add two degrees of freedom to the retractor. At the end of the supporting shaft is the retracting end which is a flat shape, slightly up curved and non-cutting tip. The retracting end adds to the retractor its last degree of freedom. There is no longitudinal axis for this retractor. However, the points H and F at the lower surface of the handle and the lower surface of the supporting shaft pass through a same horizontal plane A.

In reference to FIG. 3, the present retractor has points H and F passing through the horizontal plane A. Two tangent lines T1 and T2 can be drawn at the curved surface of the retracting end near point F, the lowest point of the supporting shaft from the side elevational view. R1 is the angle between T1 and plane A, and R2 is the angle between T2 and plane A. The preferred angle R1 is between 20 and 40 degrees, and the preferred angle R2 is between 40 and 60 degrees. Two tangent lines T3 and T4 can be drawn at the convex surface of the handle near point H, the lowest point of the handle from the side elevational view. S1 is the angle between T3 and plane A, and S2 is the angle between T4 and plane A. The preferred angle S1 is between 10 and 30 degrees, and the preferred angle S2 is between 40 and 60 degrees.

Two angles S1 and S2 are formed to specify the curvature of said convex surface for said handle. Two angles R1 and R2 are formed to specify the curvature of said retracting end.

Figure 4:
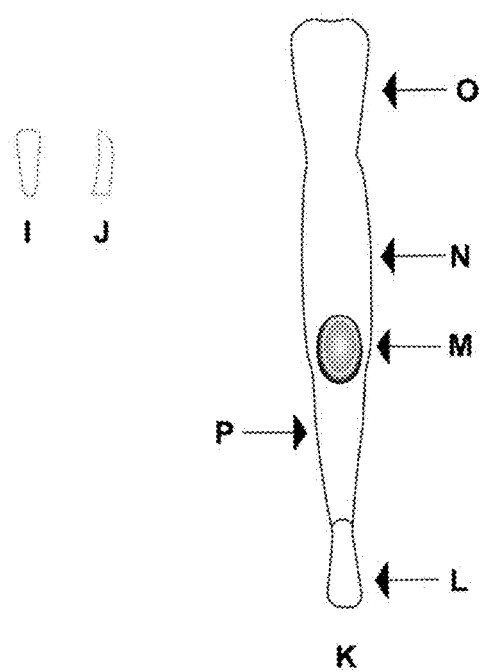
FIG. 4 I and J show the fragmentary plan view of the retracting end.

The fragmentary plan view of the retracting end and the top plan view of the present retractor are shown in FIG. 4. Top view of the retracting end has a flat shape and a non-cutting tip. The side view of the retracting end shows a slightly curved and convex non-cutting end. There are neither sharp edges nor corners at this retracting end. Top plan view of the retractor gives a general illustration of the retractor and parts. The retractor is made as one single unit.

Figure 5:
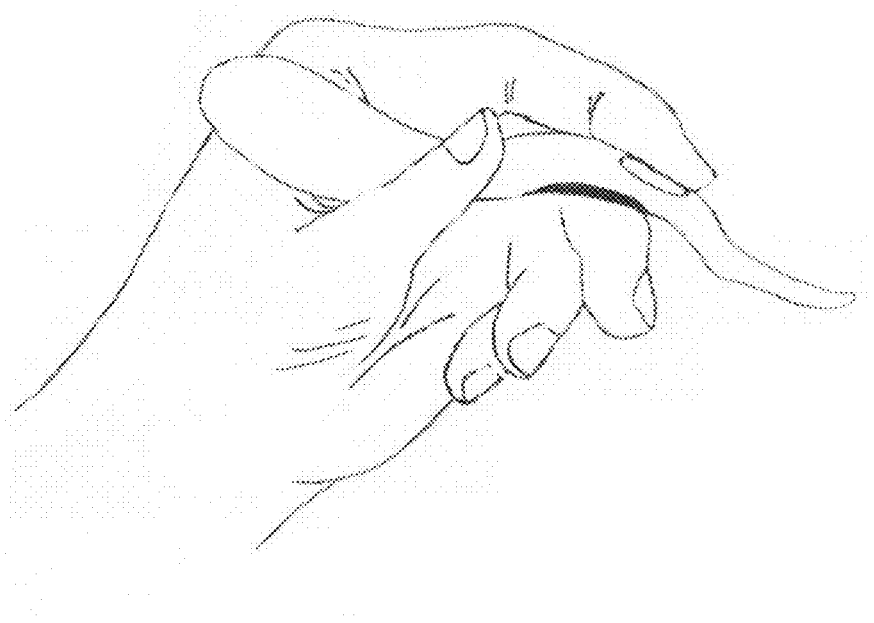
FIG. 5 is a variation of the present retractor with an internal housing incorporated at the integral part of the supporting shaft. This internal housing is able to accept ends from various instruments. Ends and tips can either be made of medical-grade stainless steel or biocompatible rigid disposable materials.

This retractor offers surgeons a more comfortable grip in handling and controlling this instrument. The present retractor has a range of angle specified at both ends, and six degrees of freedom in its design from the handle to the retracting end. The advantages of this design are to enable access at the surgical site to retract and stabilize specific tissue without damaging adjacent tissue or organs, and to provide its users improved precision in utilizing this retractor. The variation of this retractor shown in FIG. 5 has the advantage of accepting various ends and tips which makes this version of the variation suitable for both right handed and left handed users.

REFERENCES CITED

| U.S. PATENT DOCUMENTS | | |
|---|---|---|
| 5,487,756 | December 1994 | Kallesoe et al. |
| 6,461,368 B2 | October 2002 | Fogarty et al. |

The invention claimed is:

1. A retractor used to assist in cuff implantation, cuff removal, retracting soft tissue, and nerve repositioning comprising:
   (a) a passive grip handle that is rounded and comfortable to fit in the hands of the user; said handle has a lower convex surface and a lowest point (H) on said lower convex surface from a side elevational view;
   (b) a main shaft extending upwardly from said handle comprising a shape having a three degrees of freedom bend along three axial planes and two finger rests, one finger rest on an upper surface of said main shaft and the other finger rest on a lower surface of said main shaft;
   (c) an integral supporting shaft extending downwardly from said main shaft and gradually transitioning to a more flat and narrow profile along three axial planes; said supporting shaft has a lower surface and a lowest point (F) on said lower surface from a side elevational view; and
   (d) a non-cutting, nontraumatic retracting end extending gently upward from a distal end of said supporting shaft at an angle, said angle specified by a first angle (R1) and a second angle (R2); wherein said retractor does not have a longitudinal axis.

2. The retractor according to claim 1, wherein said retractor is one single unit without adapting or connecting parts.

3. The retractor according to claim 1, wherein two tangent lines (T3) and (T4) are drawn from said lower convex surface of said handle; said tangent lines (T3) and (T4) and a horizontal plane (A) passing said lower surface of said handle and said lower surface of said supporting shaft, forming two angles (S1) and (S2), respectively.

4. The retractor according to claim 3, wherein said angle (S1) is configured between 10 and 30 degrees and said angle (S2) is configured between 40 and 60 degrees; said angles (S1) and (S2) specify a curvature for said lower convex surface of said handle.

5. The retractor according to claim 1, wherein two tangent lines (T1) and (T2) are drawn from a lower surface of said retracting end; said tangent lines (T1) and (T2) and a horizontal plane (A) passing said lower surface of said handle and said lower surface of said supporting shaft, forming the angles (R1) and (R2), respectively.

6. The retractor according to claim 5, wherein said angle (R1) is configured between 20 and 40 degrees and said angle (R2) is configured between 40 and 60 degrees; said angles (R1) and (R2) specify a curvature for said lower surface of said retracting end.

7. The retractor according to claim 1, wherein a profile of said retractor has a minimum of three degrees of freedom in its design.

8. The retractor according to claim 1, wherein said retracting end has neither sharp edges nor corners; and wherein a top view of said retracting end is flat.

9. The retractor according to claim 1, wherein said retracting end is convex and curves gently upward from a side elevational view.

10. The retractor according to claim 1, wherein said retractor has a minimum length of 12 cm and said retractor is configured to offer control and precision to users.

11. The retractor according to claim 1, wherein said handle is configured to have a diameter between 12 mm and 16 mm.

12. The retractor according to claim 1, wherein said main shaft is configured to have a diameter between 9 mm and 12 mm.

13. The retractor according to claim 1, wherein said handle is rounded; said handle is configured to rest between a thumb and an index finger such that said rounded handle fits passively.

14. The retractor according to claim 1, wherein said main shaft is configured to fit comfortably between an index finger and a middle finger; and wherein said retractor is configured to improve visualization at a surgical site.

15. The retractor according to claim 1, wherein said non-cutting, nontraumatic retracting end has a shape without sharp edges on all sides and without corners.

16. The retractor according to claim 1, wherein a horizontal plane (A) passes through said lowest point (H) on said lower convex surface of said handle and said lowest point (F) on said lower surface of said supporting shaft.

* * * * *